United States Patent [19]

Kaersgaard

[11] Patent Number: 5,245,014
[45] Date of Patent: Sep. 14, 1993

[54] METHOD FOR ISOLATING FACTORS VIII FROM PLASMA BY GEL FILTRATION CHROMATOGRAPHY UNDER GROUP SEPARATION CONDITIONS

[75] Inventor: Per Kaersgaard, Vedbaek, Denmark

[73] Assignee: Novo Nordisk A/S, Bagsvaerd, Denmark

[21] Appl. No.: 610,480

[22] Filed: Nov. 7, 1990

[30] Foreign Application Priority Data

Nov. 9, 1989 [DK] Denmark .............. 5621/89

[51] Int. Cl.$^5$ .............................................. C07K 3/12
[52] U.S. Cl. .................................. 530/383; 530/381; 530/417
[58] Field of Search .............. 530/381, 382, 383, 384, 530/417

[56] References Cited

U.S. PATENT DOCUMENTS

| | | | |
|---|---|---|---|
| 4,495,175 | 1/1985 | Chavin et al. | 530/383 |
| 4,543,210 | 9/1985 | Mitra et al. | 530/383 |
| 4,675,385 | 6/1987 | Herring | 530/383 |
| 4,758,657 | 7/1988 | Farb et al. | 530/383 |
| 4,814,435 | 3/1989 | Schwarz et al. | 530/383 |
| 4,831,119 | 5/1989 | Nordfang et al. | 530/383 |
| 4,847,362 | 7/1989 | Mathews et al. | 530/383 |

FOREIGN PATENT DOCUMENTS

| | | |
|---|---|---|
| 0104356 | 4/1984 | European Pat. Off. |
| 0321835 | 6/1989 | European Pat. Off. |
| WO89/09784 | 10/1989 | PCT Int'l Appl. |

OTHER PUBLICATIONS

J. Chrom., 326 (1985) 217-224, Isolation of Human Factor VIII:C By Preparative High-Performance Size-Exclusion Chromatography, S. W. Herring, K. T. Shitanishi, K. E. Moody and R. K. Enns.
Ratnoff et al. (1969) J. Clin. Invest. 48:957-962.
Ratnoff et al. (1968) J. Lab. Clin. Med. 72(6):1007-1008 (abstract).
Paulssen et al. (1969) Thromb. Diathes. Haemorr 22:577-583.
Cooper (1977), "The Tools of Biochemistry", Wiley, N.Y., pp. 187-189.
Dengler et al. (1990) Vox Sang. 58:257-263.
Timmons et al. (1978) Thrombosis Res. 12:297-306.
Dengler et al. (1990) Vox Sang. 58(4):257-263 (abstract).
te Booy et al. (Mar. 9, 1990) J. Chromatogr. 503(1):103-114 (abstract).

*Primary Examiner*—Robert A. Wax
*Assistant Examiner*—Richard C. Ekstrom
*Attorney, Agent, or Firm*—Steve T. Zelson; Elias J. Lambiris

[57] ABSTRACT

A method for isolating Factor VIII from other proteins dissolved in blood plasma is disclosed, wherein plasma is subjected to gel filtration under group separation conditions giving a fraction containing Factor VIII in very high yield and almost free of other proteins.

6 Claims, 2 Drawing Sheets

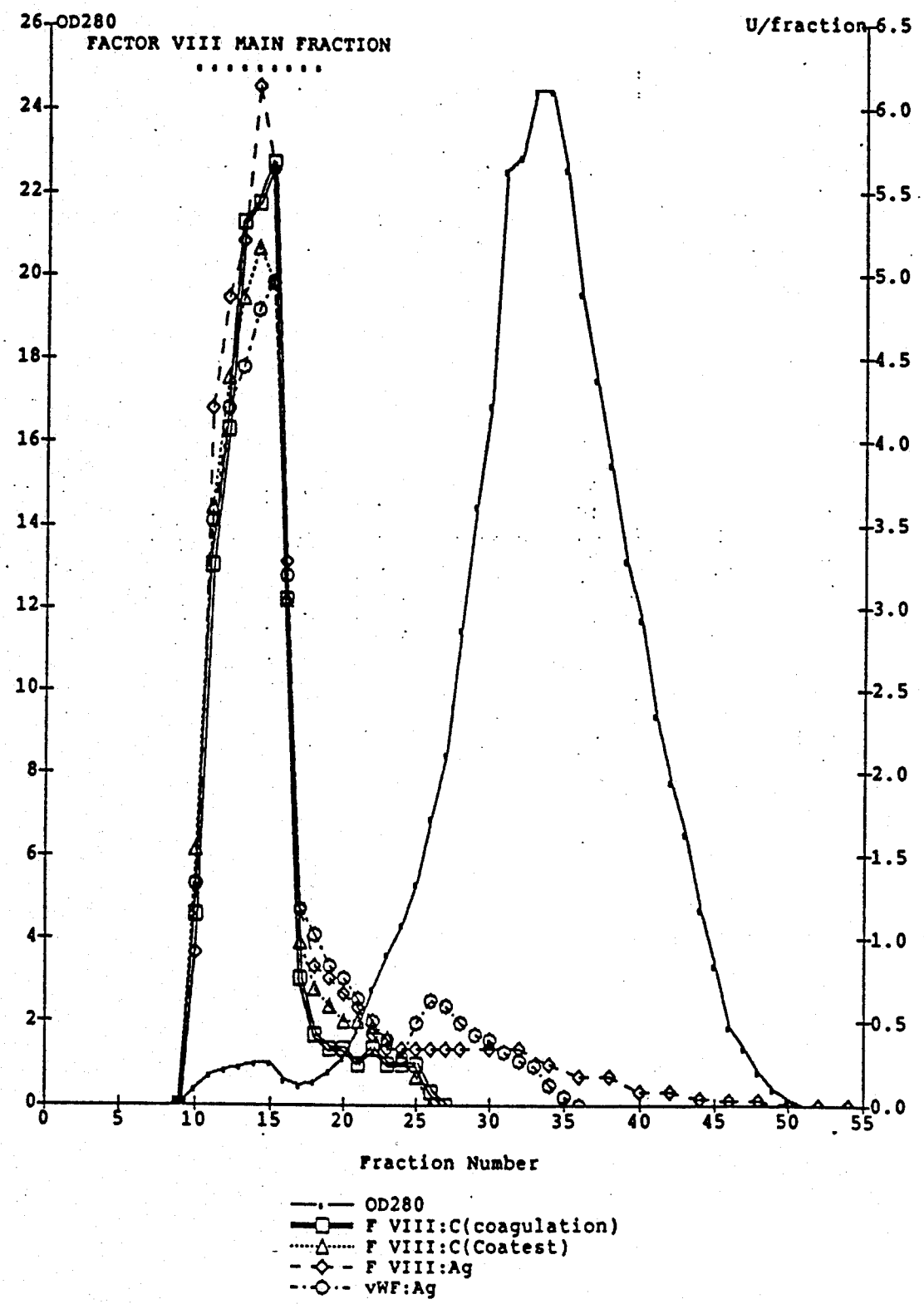

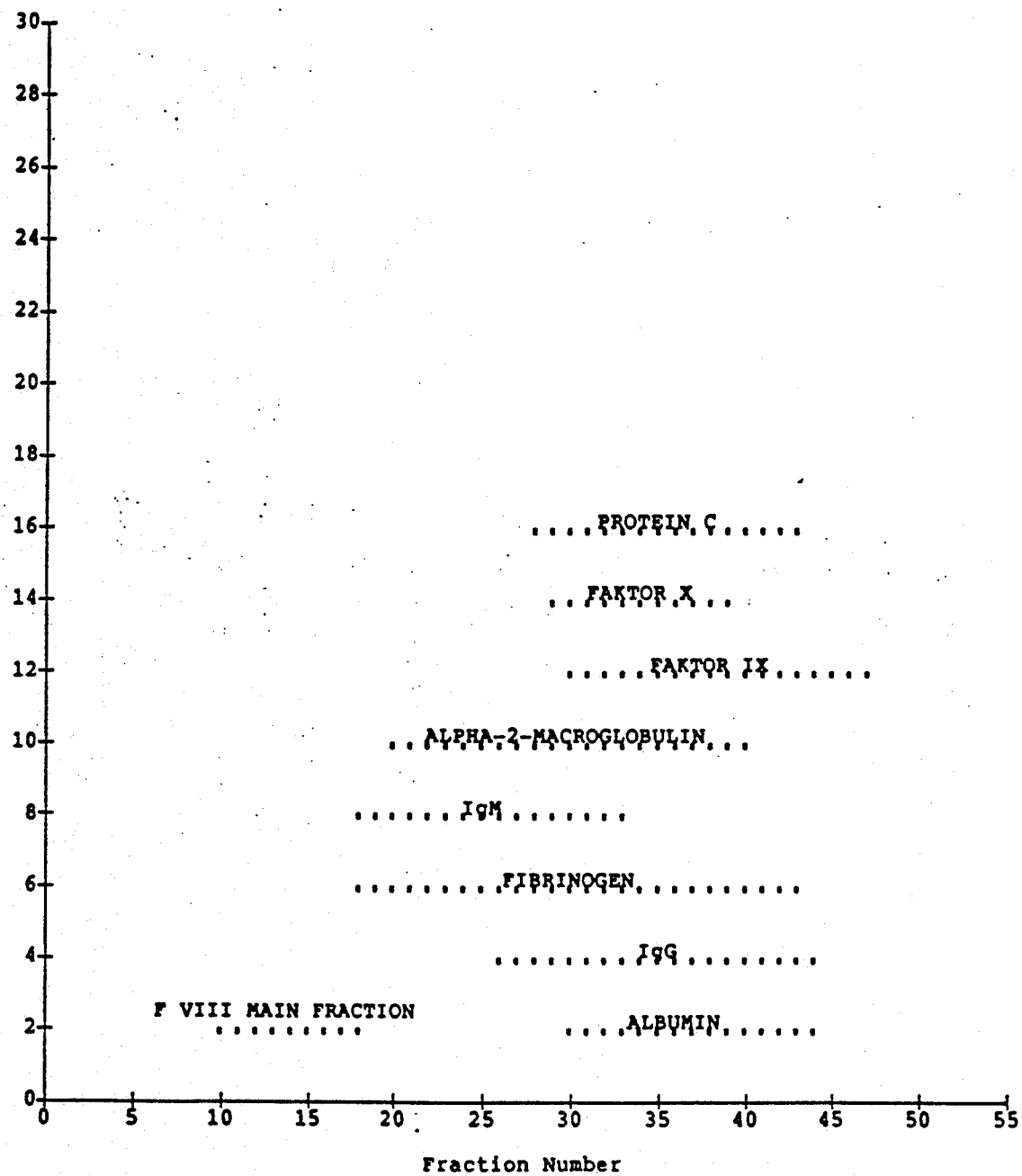
FIG.2. ELUTION OF VARIOUS PROTEINS.

METHOD FOR ISOLATING FACTORS VIII FROM PLASMA BY GEL FILTRATION CHROMATOGRAPHY UNDER GROUP SEPARATION CONDITIONS

The present invention relates to a method for isolating biological compounds such as proteins, especially coagulation factor VIII, from body fluids such as plasma using gel filtration as a first isolating step.

BACKGROUND OF THE INVENTION

Factor VIII also known as antihaemophilic factor A or AHF is a plasma protein that participates in the intrinsic pathway of blood coagulation.

Factor VIII circulates in the blood plasma in an extreme low concentration in the form of a non-covalent complex of two proteins having Factor VIII coagulant activity (Factor VIII:C) and ristocetin co-factor activity (von Willebrand Factor(vWF)), respectively, said complex having a molecular weight of $1-20 \times 10^6$ D.

Factor VIII:C is absent or defective in individuals suffering from the bleeding disorder Haemophilia A affecting about 5 out of 100,000 persons.

von Willebrand Factor binds to activated platelets in such a manner that the aggregation of the activated platelets is enhanced. This effect may be detected in vitro by aggregation of ristocetin induced platelets. Along with von Willebrands disease a prolonged bleeding time is seen due to the lack of or reduced level of biological activity of von Willebrand Factor.

Haemophiliacs suffering from haemophilia A and patients suffering from severe cases of von Willebrands disease are today treated with concentrates comprising Factor VIII:C/vWF, a treatment which has improved their quality of life and economic capacity considerably and has contributed to an increased length of life for these patients.

Pharmaceutical preparations containing Factor VIII (Factor VIII:C and/or vWF) may be produced from blood or blood plasma. The production of such preparations may be carried out in various known manners, all of which are characterized by low yields of especially Factor VIII:C. Common to nearly all the methods is an initial purification step comprising a cryoprecipitation. By cryoprecipitation frozen plasma is thawed at a temperature of 0°-4° C. which gives rise to a precipitate comprising Factor VIII which may be collected by e.g. centrifugation. Even though the cryoprecipitation is relatively simple it has an essential drawback because when used in larger scale, i.e. pools of plasma comprising more than 5 kg, it gives a low yield of Factor VIII:C (30-45% of the contents of plasma), which means that the final yield is low irrespective of which downstream purification steps are used.

Furthermore, in general a virus inactivating step has been included during the production of Factor VIII preparations. The virus inactivating steps have increased the safety against virus of the preparations considerably but causes in most cases a further reduction of the yield of Factor VIII:C.

The very low overall yields of Factor VIII have lead to a shortage of these preparations on several locations and thus, there is a need of new methods for purifying Factor VIII in high yield to comply with the demand of Factor VIII for the treatment of haemophiliacs.

New methods for isolating Factor VIII directly from plasma in high yield would be of great interest as up to 70% of the contents of Factor VIII in plasma is lost as early as in or before the cryoprecipitation.

Recently it has been tried to isolate Factor VIII directly from plasma using affinity chromatography (Thromb. Haemost., 61,(2), 234-237(1989)) but only a yield of less than 60% and a specific of 1 IU Factor VIII/mg protein of the isolated Factor VIII-containing fraction was obtained.

Gel filtration also named gel permeation chromatography or size exclusion chromatography is a diffusion controlled process that is used for separating solutes according to their size. The solutes are passed through a column packed with inert porous gel particles having a pore size excluding the largest molecules whereas the smaller molecules diffuses into the stationary phase inside the gel particles. Thus, the largest molecules being totally excluded from the gel particles are eluted first with the "void volume", whereas the smaller molecules spend a longer time passing the column and are eluted according to decreasing size with increasing "elution volumes".

Gel filtration may be carried out in two different manners:

1. Group Separation Mode

In the group separation mode the solutes are separated in two groups having great difference in their molecular sizes, one group being eluted with the void volume and the other group being eluted later with a much larger elution volume often close to the total "bed volume"; this procedure is primarily used to separate proteins from dissolved salts or to exchange buffer and is referred to as "desalting". For "desalting" rigid gels having a small pore size is used and the process may be carried out using large amounts of material (sample volumes constituting 20-30% of the bed volume) and using a high flow rate (about one bed volume of buffer per hour); thus, the capacity of the column will be large.

2. Fractionation Mode

In the fractionation mode the solutes having similar molecular weight are separated; this procedure is often used for separating proteins. For this purpose, gel particles having larger pores are used and the gel filtration medium is chosen so as to ensure that the proteins are eluted between the void volume and an elution volume corresponding to the total bed volume. The substances are eluted more closely than when using group separation conditions and may overlap. High flow rates are furthermore not desirable because this does not allow for an effective separation of proteins, and the column load must be kept low in order to obtain a reasonable separation of the individual proteins. Thus, gel filtration used in the fractionation mode has only been recommended for separation of proteins as a last polishing step where the volume to be fractionated is small (Jagschies, Ullmanns Encyclopedia of Industrial Chemistry, vol B3(10), 1988 and Bio/Technol., 4, 954-58(1986)).

It has been tried to isolate Factor VIII from plasma using gel filtration (J. Lab. Clin. Med., 72, (6), 1968, 1007-1008 and J. Clin. Invest., 4s, 1969, 957-962). A great purification was found during the experiments but the yields were only about 40-50%. The purity of the resulting Factor VIII-containing fraction was found to be dependent on the starting plasma, as a great content of lipids and chylomicrons gave rise to a turbid Factor VIII fraction having lower specific activity. It was noted that the gel filtration technique used did not allow handling of large amounts of plasma even though preliminary experiments indicated that gel filtration of the much more concentrated Cohn fraction I seemed possible.

Furthermore, Paulssen et. al. (Thromb. Diathes. Haemorr., 22, 1969, 577-583) found that Factor VIII might be separated from other plasma proteins using the gel medium Sepharose 6B but that chromatography using gel filtration only seemed possible in large scale when redissolved cryoprecipitate was used as starting material.

U.S. Pat. No. 3,637,489 discloses a process for separating blood components using gel filtration and using porous glass beads. The process is especially intended for separation of immunologically active materials from other constituents in serum or plasma.

Since then several attempts to utilize gel filtration for purifying Factor VIII have been carried out, but the attempts have concentrated on gel filtration of partially purified fractions of plasma (redissolved cryoprecipitate and further purified fractions thereof). All attempts were carried out using either small loads of the columns and/or small flow rates or combinations thereof.

Gel filtration as a method for protein fractionation has been known since 1959 and is widely used in biochemical research laboratories as a method for characterization of proteins and for purification of proteins from samples with small volumes, e.g. less than 1 liter. Gel filtration has up to the present invention not been used on a large scale in plasma fractionation for protein separation, the only use being desalting of ethanol and salts from albumin solutions. Thus, as stated in reference books: "The main reason why gel filtration has not become a major technique in plasma fractionation are the low throughput of protein per column volume" (J. H. Berglof: "Fractionation by Gel Filtration", p. 163-173 in J. M. Curling (Ed.): "Methods of Plasma Protein Fractionation", Academic Press, London, 1980) and "Unfortunately, the protein masses that can be handled by reasonably sized columns are small, and the dilution of the sample cannot be neglected. The method is therefore not much used in plasma fractionation" (J. J. Morgenthaler et. al.: "Preservation of structure and function during isolation of human plasma proteins", p. 127-138 in Smit Sibinga et. al. (Eds.): "Plasma Fractionation and Blood Transfusion", Martinus Nijhoff Publishers, Boston, 1985).

U.S. Pat. No. 4,675,385 discloses a process for isolating Factor VIII procoagulant protein from a plasma preparation comprising Factor VIII, high molecular weight constituents and low molecular weight constituents by sequential high performance size exclusion chromatography by preparing, in a first step, a buffered aqueous composition of a plasma preparation and separating the low molecular weight constituents by introducing the composition on a chromatographic column of porous high performance liquid chromatography beads having a size from about 13 microns to about 35 microns and eluting the column with a buffered aqueous eluant. In order to have a good separation U.S. Pat. No. 4,675,385 teaches the use of columns having an aspect ratio not lower than between 10 and 40 which reduces the capacity but does not ensure a good separation of Factor VIII constituents from low molecular weight plasma proteins However, this first isolation does not ensure a good separation of proteins showing Factor VIII:C activity from other protein constituents of the plasma preparation which is only obtained by carrying out the second HPLC.

Thus, it has up to the present invention been a generally accepted fact, that gel filtration is not a suitable method for protein separation in plasma fractionation, when handling larger volumes, e.g. above 5 liters.

It has now surprisingly been found that when selecting gel filtration materials being designed for high flow rates it is possible to isolate Factor VIII in the form of a pure fraction and in a very high yield directly from plasma by very gentle mechanical separation without having to rely on the normal initial cryoprecipitation.

BRIEF DESCRIPTION OF THE INVENTION

The present invention relates to a method for isolating Factor VIII in the form of a complex of Factor VIII:C and vWF from other proteins in blood plasma using gel filtration.

The method of the invention is characterized in that isolated plasma or thawed freshly frozen plasma is subjected to gel filtration under group separating conditions using a high load and a high flow rate, the gel filtration medium being constituted of particles being inert to Factor VIII and having a fractionation range in the interval from $1 \times 10^3$ to $1 \times 10^8$ more preferred from $1 \times 10^4$ to $8 \times 10^7$. The fractionation range may e.g. be in the interval from $5 \times 10^4$ to $4 \times 10^7$.

In a preferred embodiment, the volume of plasma added is at least 5% of the bed volume. The amount of plasma added is preferably 15-40% of the bed volume.

The method to the invention is preferably carried out using a flow rate of at least 0.3 bed volumes per hour, most preferred 0.5-2 bed volumes per hour.

For the purpose of the present invention a gel filtration medium having a rigidity allowing for a quick elution is used. Furthermore, the gel must be chemically and immunologically inert to Factor VIII during the gel filtration. Experiments have shown that the method of the present invention may be carried out using commercial gels like Sepharose CL-4B, Sepharose CL-6B, Sepharose 4FF, Sepharose 6FF, Sephacryl S-400, Sephacryl S-500, Fractogel TSK HW-65(F) and Matrex Cellufine CGL 2000 all being appropriate for the purpose of the present invention. Such gels are generally of a particle size (wet) in the interval from about 32 $\mu$m to about 200 $\mu$m.

According to one embodiment of the method of the present invention frozen plasma is thawed and it is ensured that all Factor VIII has been dissolved whereafter the thawed plasma is preferably added to the column immediately after all Factor VIII has been dissolved. The temperature is preferably not allowed to rise too high to avoid too extensive degradation of Factor VIII. The plasma may be pretreated by adding e.g. heparin, citrate, sucrose, amino acids, salts or other stabilizers and optionally filtered, centrifugated, concentrated by ultrafiltration, pre-precipitated using usual precipitating agents, or pretreated in another manner before adding the same to the column as long as any optional pretreatment does not have any significant influence on the contents of Factor VIII of the plasma.

The method to the invention has surprisingly shown to give a very high yield of Factor VIII. Typically above 70% of the contents of Factor VIII of the plasma is retrieved in the product, and the method gives rise to very pure products having a specific activity of from 1 to about 4 IU Factor VIII:C/mg protein. This may partially be ascribed to the fact that using the method of the invention Factor VIII is also separated from proteolytic enzymes which may normally cause a breakdown of Factor VIII:C very early in the isolation process.

The method of the invention enables the treatment of large amounts of plasma under conditions where the plasma is applied using high loads and high flow rates in a gel filtration giving rise to a very high retrieval of Factor VIII in high purity. Thus a very efficient method having industrial applicability is offered.

The Factor VIII containing fraction(s) from the gel filtration or the combined fractions from more gel filtrations may then be concentrated and further purified using techniques known per se such as ultrafiltration, precipitations, ion exchange, affinity chromatography or the like.

The remaining plasma proteins such as albumin, immunoglobulins, the prothrombin complex, antithrombin III and others may also be isolated from the later fractions of the gel filtration using techniques known per se, such as precipitation with alcohol, PEG-precipitations, chromatography or the like.

The determination of Factor VIII:C-activity may be carried out using either a two-stage assay or one-stage assay. It is an established fact that one-stage and two-stage assays may result in differing determinations of the Factor VIII:C activity in a sample. Furthermore, it is known that repeated determinations using the same assay on the same sample may give rise to variations in the determination of the Factor VIII:C activity.

As used herein the expression "plasma" means blood from which all blood corpuscles and platelets have been removed e.g. by centrifugation.

"Factor VIII:Ag" denotes Factor VIII related antigen, and "vWF-Ag" von Willebrand Factor related antigen.

The "bed volume" is defined as the volume of the packed gel media and the interstitial liquid. "Void volume" is defined as the volume of buffer between the gel particles, and "elution volume" is the volume of buffer used to elute a specific material. The expression "column load" is used to designate the volume of material added to the bed, calculated as a percentage of the bed volume. The expression "fractionation range" is intended to designate the range of molecular weights of (globular) proteins or larger molecules for which the gel material is recommended by the supplier.

The method of the invention is further explained with reference to the drawings and the Examples elucidating embodiments of the invention. The Examples are for illustrative purpose only and are not to be construed as limiting the scope of the invention which is defined by the appended claims.

BRIEF DESCRIPTION OF THE DRAWINGS

The present invention is further illustrated by reference to the accompanying drawings in which FIG. 1 shows a graph illustrating the elution of Factor VIII by gel filtration in accordance with the present invention determined by different assays, and FIG. 2 illustrates the order of elution of various plasma proteins by gel filtration in accordance with the invention.

EXPERIMENTAL PART

EXAMPLE 1

Gel Filtration of Plasma to Isolate Factor VIII

A column of $\phi$ 2.6 cm was packed with Sepharose CL-4B to a final height of 60 cm.

Frozen plasma from a Danish blood bank was thawed to 25° C. on a water bath. After adding 1 IU heparin/ml, 50 ml (16% of the bed volume) of plasma was added to the column using a flow of 100 ml/hr whereafter the column was eluted using a forced flow of 200 ml/hr buffer corresponding to 0.63 bed volume per hour. The equilibration of the column and the elution were carried out using a buffer, 0.02 M citrate, 0.15 M NaCl, pH. 7.4. To the buffer was furthermore added 2.55 ml 1 M $CaCl_2$ per liter giving a free calcium ion ($Ca^{2+}$) concentration of about $7 \times 10^{-5}$ cm. The free calcium ion concentration was checked using a calcium selective electrode from Ingold GmbH (Frankfurt/Main, FRG). Fractions were collected, and for each fraction $OD_{280}$, Factor VIII:C (using both one-stage coagulation assay and two-stage chromogenic assay), Factor VIII:Ag, albumin, IgG, fibrinogen, IgM, alpha-2-macroglobulin, Factor IX, Factor X, protein C and antithrombin III were determined. Protein as measured by $OD_{280}$ was eluted with a little peak at void volume (fractions 10–18), followed by a very big broad peak (fractions 19–50, cf FIG. 1). 82% of the Factor VIII:C activity as determined by two-stage and 91% of the Factor VIII:C activity as determined by one-stage coagulation assay was eluted in one aggregate peak with the void volume (the Factor VIII-main fraction) together with the earliest small protein peak. The remainder of Factor VIII was eluted in a minor subsequent peaktail immediately subsequent to the Factor VIII-main fraction (fractions 19–26). Factor VIII:Ag and vWF:AG were eluted together with Factor VIII:C but having somewhat broader subsequent peaktails.

All other plasma proteins being determined were eluted in the fraction after the Factor VIII-main fraction together with the large broad protein peak (vide FIG. 2). The plasma proteins being separated from Factor VIII:C are of the following molecular weights:

| | |
|---|---|
| Antithrombin III: | 65,000 D |
| Protein C: | 62,000 D |
| Factor X: | 59,000 D |
| Factor IX: | 57,000 D |
| Alpha-2-macroglobulin: | 718,000 D |
| IgM: | 900,000 D |
| Fibrinogen: | 340,000 D |
| IgG: | 150,000 D |
| Albumin: | 67,000 D |

The determination of Factor VIII:C-activity using the two-stage chromogenic assay was carried out using the chromogenous substrate method (KABI Coatest Factor VIII), the original method using test tubes at 37° C. being modified to be carried out using microtiter plates with reduced use of reagents. A 50 microliter sample or standard is used which after mixing with 75 microliters of a solution of phospholipid, Factor IXa, Factor X and $CaCl_2$ is incubated at 37° C. for 15 minutes, whereafter 50 microliters of substrate is added. After a further 20 minutes incubation at 37° C., the reaction is quenched by adding 50 microliters 1 M citric acid. The color development is read at 405 nm the reference being at 492 nm.

The determination of the factor VIII:C activity using the one-stage assay is carried out using the APTT-method (Activated Partial Thromboplastin Time). 100 microliters sample or standard is pipetted into the cuvettes whereafter 100 microliters deficient plasma (Factor VIII deficient plasma, General Diagnostic) is added, and the solution is thermostated at 37° C. for 5 minutes After addition of 100 microliters 0.03 M $CaCl_2$ the time until the coagulation of the solution is determined.

For quantitative determinations calibration curves based on dilution series of an internal standard being calibrated against WHO standard (3rd Int. Standard of FVIII, Human Plasma, 3.9 IU/ml) are produced. The two-stage assay as described herein has a lower (about 10 times) detection limit than the one-stage assay. When adding heparin it is an advantage to use the two-stage assay, as any possible influence of heparin on the assay may be removed more easily by dilution.

Factor VIII:Ag was determined using ELISA using antibodies from a Factor VIII inhibitor patient as coating material on microtiter plates (Nunc, Kamstrup, 4000 Roskilde, Denmark) and using peroxidase labelled F(AB')$_2$ fragments from the same inhibitor patient for determining bound Factor VIII (Thromb. Haemost., 53(3), 1985, 346-350). Standard curves were produced using pooled normal plasma calibrated against a WHO standard (1st IRP, established 1982).

vWF:Ag was also determined using ELISA, but using a rabbit anti-human vWF (DAKO, Denmark) as coating material and peroxidase labelled rabbit anti-human vWF (DAKO, Denmark) for determining bound vWF. Standard curves were produced using the same normal plasma as for Factor VIII:Ag ELISA.

Factor IX was determined using one-stage coagulation assay in an analogous manner as Factor VIII:C only using Factor IX deficient plasma. IgG was determined using radial immunodiffusion (Immunochemistry, 2, 1965, 235-254), and albumin, fibrinogen, alpha-2-macroglobulin, Factor X, protein C and anti-thrombin III were determined using rocket immunoelectrophoresis (Anal. Biochem., 15, 1966, 45-52). $OD_{280}$ was determined using a spectrophotometer (Spectronic 601 from Milton Roy Company), and protein using Kjeldahl was determined according to Ph. Eur. 2nd. Ed., I, V.3.5.2 without precipitation with TCA. Specific activity of purified fractions was calculated as the ratio of the Factor VIII:C concentration either to the $OD_{280}$ or to the concentration of protein as determined using Kjeldahl. When using $OD_{280}$ for calculating the specific activity, the results of different experiments are not directly comparable, unless when using the same starting plasma, as the fraction containing Factor VIII is often turbid, vide the results of Ratnoff et. al. (J.Clin. Invest., 48, 1969, 957-962).

The various gel filtration media used in the experiments were from the following sources: Sepharose CL-6B, Sepharose CL-4B, Sepharose CL-2B, Sepharose 6FF, Sepharose 4FF, Sephacryl S-400, and Sephacryl S-500 were all from Pharmacia (Hillerød, Denmark), Biogel A-5m, Fine was from BioRad (Bie & Berntsen, Rødovre, Denmark), Fractogel TSK HW-65(F) was from Merck (Struers, Rødovre, Denmark) and Matrex Cellufine GCL 2000 was from Amicon (Helsingborg, Sweden).

EXAMPLE 2

Gel Filtration of Plasma to Isolate Factor VIII Using Various Gel Filtration Media.

A column of φ 2.6 cm was packed with various gel filtration media having different fractionation range and different structure. In all cases the final height of the packed bed was 60 cm. Plasma was thawed as described in Example 1 and 1 IU of Heparin per ml. was added. For each of the gel filtration media, the column was loaded with 50 ml. of plasma (16% of the bed volume). The loading of the column and elution with buffer was carried out as described in Example 1. The flow rate was in all cases the same as stated in Example 1, except for the experiment using Biogel A-5m, where the flow rate was lowered to 50 ml/hour due to increased backpressure. Fractions were collected, and for each fraction $OD_{280}$ and Factor VIII:C, using Coatest, were determined. The specific activity of the Factor VIII-main fraction was calculated as the ratio of Factor VIII:C/ml to $OD_{280}$. The experiments were repeated n times using different plasmas for each load and mean values of yield and specific activity were calculated. The Factor VIII-main fraction was selected in the same manner as described in Example 1, and the yield is stated as the contents of Factor VIII:C in the Factor VIII-main fraction as a percentage of the contents of Factor VIII:C of the added plasma.

The fractionation range and particle size for the various media and the calculated mean values are stated in the below Table I.

TABLE I

| Gel fil. medium | Fractionat. Range MW | Number of Exp. n | Yield in % | Spec. Activity | Particle wet diam. in μm |
|---|---|---|---|---|---|
| A | $1 \times 10^4$–$4 \times 10^6$ | 3 | 95 | 0.16 | 40–165 |
| B | $6 \times 10^4$–$2 \times 10^7$ | 4 | 82 | 0.88 | 40–165 |
| C | $7 \times 10^5$–$4 \times 10^7$ | 3 | 68 | 0.24 | 60–200 |
| D | $1 \times 10^4$–$4 \times 10^6$ | 3 | 96 | 0.71 | 40–165 |
| E | $6 \times 10^4$–$2 \times 10^7$ | 3 | 86 | 1.35 | 40–165 |
| F | $6 \times 10^4$–$8 \times 10^7$ | 3 | 91 | 0.28 | 40–105 |
| G | $1 \times 10^4$–$5 \times 10^6$ | 1 | 71 | 0.12 | 40–80 |
| H | $5 \times 10^4$–$5 \times 10^6$ | 2 | 84 | 0.18 | 32–63 |
| I | $1 \times 10^4$–$3 \times 10^6$ | 2 | 92 | 0.18 | 45–105 |
| J | $1 \times 10^4$–$8 \times 10^6$ | 3 | 101 | 0.75 | 40–105 |

A: Sepharose CL-6B;
B: Sepharose CL-4B;
C: Sepharose CL-2B;
D: Sepharose 6FF;
E: Sepharose 4FF;
F: Sephacryl S-500;
G: Biogel A-5m Fine;
H: Fractogel TSK HW-65 (F);
I: Matrex Cellufine GCL 2000;
J: Sephacryl S-400

EXAMPLE 3

Gel Filtration of Plasma to Isolate Factor VIII Using Various Column Loads

A column of φ 2.6 cm was packed with Sepharose 4FF to a final height of 60 cm. Plasma was thawed ad described in Example 1. After thawing, pH of the plasma was adjusted to 7.0 using 0.5 M HCl, 1 IU heparin per ml. was added, and the plasma was filtered through a 10 micrometer nylon filter. To the column was added 30 ml, 40 ml, 50 ml, 60 ml, and 70 ml plasma, respectively. The addition, flow, and elution using buffer was carried out as described in Example 1, through the buffer was adjusted to pH 7.0. Fractions were collected, and for each fraction $OD_{280}$ and Factor VIII:C using Coatest were determined. Specific activity of the Factor VIII-main fraction was calculated as the ratio of Factor VIII:C/ml to $OD_{280}$. The experiments were repeated three times using three different plasmas for each load and mean values (x) were calculated. The volume of the Factor VIII-main fraction (ml) is the volume of the fraction containing Factor VIII which can be collected before the large broad protein peak ($OD_{280}$) is eluted and is selected in the same manner as described in Example 1. The yield is stated as the contents of Factor VIII:C in the Factor VIII-main Fraction as a percentage of the contents of Factor VIII:C of the added plasma.

The calculated figures are stated in Table II below.

TABLE II

| Added amount of Plasma | | Port. No. | Factor VIII main fraction in ml | Yield in % | Specific activity |
|---|---|---|---|---|---|
| in ml | in % of bed volume | | | | |
| 30 | 9.4 | 1 | 70 | 88 | 0.81 |
| | | 2 | 70 | 95 | 0.18 |
| | | 3 | 70 | 90 | 0.63 |
| | | x | 70 | 91 | 0.54 |
| 40 | 12.6 | 1 | 70 | 76 | 0.68 |
| | | 2 | 70 | 85 | 0.17 |
| | | 3 | 70 | 93 | 0.61 |
| | | x | 70 | 85 | 0.49 |
| 50 | 15.7 | 1 | 80 | 91 | 0.57 |
| | | 2 | 80 | 90 | 0.20 |
| | | 3 | 80 | 85 | 0.53 |
| | | x | 80 | 89 | 0.43 |
| 60 | 18.8 | 1 | 80 | 79 | 0.81 |
| | | 2 | 80 | 85 | 0.16 |
| | | 3 | 90 | 95 | 0.61 |
| | | x | 83 | 86 | 0.53 |
| 70 | 22.0 | 1 | 80 | 85 | 0.82 |
| | | 2 | 100 | 90 | 0.21 |
| | | 3 | 100 | 93 | 0.53 |
| | | x | 93 | 89 | 0.52 |

EXAMPLE 4

Gel Filtration of Plasma to Isolate Factor VIII Using Various Elution Rates

To the same column as used in Example 3 was added 50 ml plasma thawed as described above. After thawing, pH of the plasma was adjusted to 7.0 using 0.5M HCl, 1 Iu heparin/ml was added, and the plasma was filtered through a 10 micrometer nylon filter. Using three different portions of plasma flow rates of 100, 200, and 300 ml/hour, respectively, were examined. The same flow was used during the addition of the plasma and the following elution. The elution was carried out using the same buffer as described in Example 3. Fractions were collected, and for each fraction $OD_{280}$ and Factor VIII:C using Coatest were determined. Specific activity and yield in the Factor VIII-main fraction were calculated as in Example 3. Mean values (x) of volume of Factor VIII-main fraction, yield and specific activity were calculated. The results are stated in Table III below.

TABLE III

| Flow | | Plasma Portion No. | Factor VIII main fract. ml | Yield in % | Specific activity |
|---|---|---|---|---|---|
| ml/hour | Bed volume per hour | | | | |
| 100 | 0.31 | 1 | 80 | 89 | 0.75 |
| | | 2 | 80 | 88 | 0.17 |

TABLE III-continued

| Flow | | Plasma Portion No. | Factor VIII main fract. ml | Yield in % | Specific activity |
|---|---|---|---|---|---|
| ml/hour | Bed volume per hour | | | | |
| | | 3 | 80 | 80 | 0.65 |
| | | x | 80 | 86 | 0.52 |
| 200 | 0.63 | 1 | 80 | 84 | 0.99 |
| | | 2 | 80 | 88 | 0.18 |
| | | 3 | 80 | 89 | 0.79 |
| | | x | 80 | 87 | 0.65 |
| 300 | 0.94 | 1 | 70 | 85 | 0.72 |
| | | 2 | 80 | 96 | 0.18 |
| | | 3 | 80 | 83 | 0.44 |
| | | x | 77 | 88 | 0.45 |

EXAMPLE 5

Gel Filtration of Plasma to Isolate Factor VIII Using Various Column Loads

A column of $\phi$ 10 cm was packed with Speharose 4FF to a final height of 60 cm. Frozen plasma from a Danish blood bank was thawed at 30° C. at a water bath. 925 grammes, 1497 grammes, and 2000 grammes, respectively were added to the column. The flow was held at about 4200 ml/hour during addition and elution of the plasma using a Masterflex hose pump (Buch & Holm, Herlev, Denmark) corresponding to about 0.89 bed volumes per hour. For elution the same buffer as described in Example 1was used. $OD_{280}$ was monitored continuously using a Pharmacia Monitor UV-1. When $OD_{280}$ started to rise at void volume, the collection of the Factor VIII main fraction was started and it was terminated, when $OD_{280}$ showed that the large protein peak started to be eluted. In the Factor VIII-main fraction the Factor VIII:C contents was determined using one-step coagulation assay, and protein was determined using Kjeldahl. The specific activity was calculated as the ratio of the total number of Factor VIII:C units in the Factor VIII-main fraction to the total number of milligrammes of protein in the Factor VIII-main fraction. The yield of Factor VIII:C was calculated as the contents of Factor VIII:C in the Factor VIII-main fraction in percent of the contents of Factor VIII:C in the plasma added.

The results are stated in Table IV below.

TABLE IV

| Added amount of plasma | | Factor VIII main fract. in grammes | Yield in % | Specific activity IU/mg |
|---|---|---|---|---|
| in grammes | % of bed volume | | | |
| 925 | 19.6 | 1192 | 74 | 2.50 |
| 1497 | 31.8 | 1860 | 73 | 2.24 |
| 2000 | 42.4 | 2200 | 81 | 1.08 |

EXAMPLE 6

Gel Filtration of Plasma to Isolate Factor VIII Using a Column of Industrial Size.

A column of $\phi$ 29 cm was packed with Sepharose 4FF. After equilibration using the same buffer as described in Example 1 the gel height was 53 cm. 10 kilogrammes of frozen plasma from a Danish blood bank was thawed and heated to 30° C., whereafter it was added to the column. The added amount constituted 28.8% of the bed volume. Using a Masterflex hose pump, a flow of 30 liters per hour corresponding to 0.86 bed volumes per hour was maintained during the addition and the elution using the equilibration buffer.

OD$_{280}$ was monitored continuously using a Pharmacia Monitor UV-1, and at the time of the first indication of a rise in the OD$_{280}$ at void volume, the Factor VIII-main fraction was collected. In total 11.73 kilogrammes Factor VIII-main fraction was collected. Then the contents of Factor VIII:C was determined using a one-step coagulation assay and protein was determined using Kjeldahl. In total 8798 IU Factor VIII:C and less than 2346 milligrammes protein were found in the Factor VIII-main fraction giving a yield of Factor VIII:C of 880 IU/kilogram plasma corresponding to 88% yield in the form of a product having a specific activity of more than 3.75 IU/milligram protein.

The Factor VIII-main fraction obtained in accordance with the method of the invention may be further purified in a manner analogous to the conventional purification of a redissolved cryoprecipitate comprising e.g. further chromatographic purification and lyophilization using usual excipients to form a stable preparation. The preparation is reconstituted before use using a convenient conventional vehicle.

I claim:

1. A method of isolating Factor VIII from blood plasma comprising (1) optionally pretreating said blood plasma and (2) subjecting said blood plasma to gel filtration column chromatography under group separation conditions, wherein the volume of blood plasma added to the column is at least 5% of the bed volume and the flow rate of blood plasma is at least 0.3 bed volumes per hour, and wherein the gel filtration medium is inert to Factor VIII and has a molecular weight fractionation range between $1 \times 10^4$ and $8 \times 10^7$.

2. The method according to claim 1, wherein the gel filtration medium has a molecular weight fractionation range between $5 \times 10^4$ and $4 \times 10^7$.

3. The method according to claim 1, wherein the volume of blood plasma added is 15–40% of the bed volume.

4. The method according to claim 1, wherein the flow rate of blood plasma is between 0.5 and 2 bed volumes per hour.

5. The method according to claim 1, wherein the gel filtration medium is a cross-linked agarose gel, a mixture of agarose and acrylic polymer, a co-polymer of oligoethyleneglycol, glycidyl methacrylate and pentaerythritol methacrylate or a cellulose gel.

6. The method according to any of claims 1, 2, 3, 4 or wherein Factor VIII is further purified by ultrafiltration, precipitation, ion exchange or affinity chromatography.

* * * * *